US007453022B2

(12) United States Patent
Mahn et al.

(10) Patent No.: US 7,453,022 B2
(45) Date of Patent: Nov. 18, 2008

(54) METHOD OF INCREASING THE CONTENT OF SELECTED TRANSGENE-CODED PROTEINS OR PEPTIDES IN PLANTS

(75) Inventors: Andreas Mahn, Bergheim (DE); Sabine Hantke, Cologne (DE); Dagmar Petsch, Cologne (DE)

(73) Assignee: Klaus Duering (DE)

( * ) Notice: Subject to any disclaimer, the term of this patent is extended or adjusted under 35 U.S.C. 154(b) by 140 days.

(21) Appl. No.: 10/500,264

(22) PCT Filed: Dec. 18, 2002

(86) PCT No.: PCT/EP02/14512

§ 371 (c)(1), (2), (4) Date: Dec. 8, 2004

(87) PCT Pub. No.: WO03/052109

PCT Pub. Date: Jun. 26, 2003

(65) Prior Publication Data

US 2005/0114926 A1 May 26, 2005

(30) Foreign Application Priority Data

Dec. 19, 2001 (EP) ................................. 01130319

(51) Int. Cl.
*C12N 15/82* (2006.01)

(52) U.S. Cl. ....................... 800/286; 800/285; 800/288; 800/294

(58) Field of Classification Search ....................... None
See application file for complete search history.

(56) References Cited

U.S. PATENT DOCUMENTS 5,702,933 A * 12/1997 Klee et al. .................. 800/283
6,891,088 B1 5/2005 Neuhaus et al.

OTHER PUBLICATIONS

Tjaden et al. Altered plastidic ATP/ADP-transporter activity influences potato (*Solanum tuberosum* L.) tuber morphology, yield and composition of tuber starch. (1998) The Plant Journal, vol. 16, pp. 531-540.*

Hausler et al. Compensation of decreased triose phosphate/phosphate translocator activity by accelerated starch turnover and glucose transport in transgenic tobacco. (1998) Planta, vol. 204, pp. 366-376.*

Bevan M. Binary Agrobacterium vectors for plant transformation. (1984) Nucleic Acids Research, vol. 12, pp. 8711-8721.*

Elomaa et al. Transformation of antisense constructs of the chalcone synthase gene superfamily into *Gerbera hybrida*: differential effect on the expression of family members. (1996) Molecular Breeding, vol. 2, pp. 41-50.*

Reiser et al. Molecular physiological analysis of the two plastidic ATP/ADP transporters from *Arabidopsis*. (2004) Plant Phys. vol. 136, pp. 3525-3536.*

Buelow, Lorenz, et al., Induction of the Maize GapC4 Promoter in Transgenic Potato under Anaerobiosis and in *Erwinia carotovora*-Inoculated . . . , Mol. Plant Microbe Interact., Mar. 1999, pp. 182-188, vol. 12, No. 3.

Cheng, Wan-Hsing, et al., Sugars modulate an unusual mode of control of the cell-wall invertase gene (Incw1) through its 3' untranslated region in, Proc. Natl. Acad. Sci. USA, Aug. 31, 1999, pp. 10512-10517, vol. 96, No. 18.

During, Klaus, et al., Transgenic potato plants resistant to the phytopathogenic bacterium *Erwinia carotovora*, Plant J., Apr. 1993, pp. 587-598, vol. 3, No. 4.

Ecker, Joseph R., et al., Plant Defense Genes are Regulated by Ethylene , Proc. Natl. Acad. Sci. USA, Aug. 1, 1987, pp. 5202-5210, vol. 84, No. 15.

Geigenberger, Peter, et al., Tuber Physiology and Properties of Starch from Tubers of Transgenic Potato Plants with Altered Plastidic Adenylate . . . , Plant Physiol., Apr. 2001, pp. 1667-1678, vol. 125, No. 4.

Goossens, Alain, et al., Co-introduction of an antisense gene for an endogenous seed storage protein can increase expression of a transgene . . . , FEBS Lett., Jul. 30, 1999, pp. 160-164, vol. 456, No. 1.

Neuhaus, Jean-Marc, et al., A Short C-Terminal Sequence is Necessary and Sufficient for the Targeting of Chitinases to the Plant Vacuole, Proc. Natl. Acad. Sci. USA, Nov. 15, 1991, pp. 10362-10366, vol. 88, No. 22.

Rocha-Sosa, Mario, et al., Both developmental and metabolic signals activate the promoter of a class I patatin gene, EMBO J., Jan. 1989, pp. 23-29, vol. 8, No. 1.

Schmitz, Udo K., et al., A Yeast Mitochondrial Presequence Functions as a Signal for Targeting to Plant Mitochondria in Vivo, Plant Cell, Aug. 1989, pp. 783-791, vol. 1, No. 8.

Sidorov, Vladimir, A., et al., Stable chloroplast transformation in potato: use of green fluorescent protein as a plastid marker, Plant J., Jul. 1999, pp. 209-216, vol. 19, No. 2.

Svab, Zora, et al., Stable Transformation of Plastids in Higher Plants, Proc. Natl. Acad. Sci. USA, Nov. 1, 1990, pp. 8526-8530, vol. 87, No. 21.

Wee, Edmund G. T., et al., Targeting of Active Sialyltransferase to the Plant Golgi Apparatus, Plant Cell, Oct. 1998, pp. 1759-1768, vol. 10, No. 10.

Geigenberger, Peter, et al., Overexpression of pyrophosphatase leads to increased sucrose degradation and starch synthesis, increased activities . . . , Planta, May 1998, pp. 428-437.

Makita, Naoko, et al., ATP/ADP switches the higher-order structure of DNA in the presence of spermidine, FEBS Lett., Oct. 29, 1999, pp. 333-337, vol. 460, No. 2.

Gaal, Tamas, et al., Transcription Regulation by Initiating NTP Concentration: rRNA Synthesis in Bacteria, Science, Dec. 19, 1997, pp. 2092-2097.

(Continued)

*Primary Examiner*—Anne Kubelilk
*Assistant Examiner*—Cathy Kingdon Worley
(74) *Attorney, Agent, or Firm*—Kelly K. Reynolds; Steven J. Hultquist; Intellectual Property/Technology Law

(57) ABSTRACT

A method of increasing the content of one or more transgene-coded proteins or peptides in a plant is described. The increase is an effect of a decrease in the concentration of an ATP/ADP transporter in the plant. The method depends on transformation with and expression of a cDNA encoding an ATP/ADP transporter operably linked in antisense orientation to a promoter active in the plant.

7 Claims, 2 Drawing Sheets

OTHER PUBLICATIONS

Artsaenko, Olga, et al., "Potato tubers as a biofactory for recombinant antibodies", "Molecular Breeding", Aug. 1998, pp. 313-319, vol. 4, No. 4.

Baeumlein, Helmut, et al., "Upstream sequences regulating legumin gene expression in heterologous transgenic plants", "Mol. Gen. Genet.", Jan. 1991, pp. 121-128, vol. 225, No. 1.

Beck, E., et al., "Nucleotide sequence and exact localization of the neomycin phosphotransferase gene from transposon Tn5", "Gene", Oct. 1982, pp. 327-336, vol. 19, No. 3.

Datla, Raju, et al., "Plant promoters for transgene expression", "Biotechnol. Annu. Rev.", 1997, pp. 269-296, vol. 3.

De Wilde, Chris, et al., "Plants as bioreactors for protein production: avoiding the problem of transgene silencing", "Plant Molecular Biology", Jun. 2000, pp. 347-359, vol. 43, No. 2-3.

Gatz, Christiane, et al., "Promoters that respond to chemical inducers", "Trends Plant Sci.", Sep. 1, 1998, pp. 352-358, vol. 3, No. 9.

Harpster, Mark H., et al., "Relative strengths of the 35S cauliflower mosaic virus, 1', 2', and nopaline synthase promoters in transformed tobacco..", "Mol. Gen. Genet.", Apr. 1988, pp. 182-190, vol. 212, No. 1.

Jones, Jonathon D.G., et al., "Expression of bacterial chitinase protein in tobacco leaves using two photosynthetic gene promoters", "Mol. Gen. Genet.", Jun. 1988, pp. 536-542, vol. 212, No. 3.

Khan, Muhammad Sarwar, et al., "Fluorescent antibiotic resistance marker for tracking plastid transformation in higher plants", "Nat Biotechnol.", Sep. 1999, pp. 910-915, vol. 17, No. 9.

Kriete, G. et al., "Male sterility in transgenic tobacco plants induced by tapetum-specific deacetylation of the externally applied . . . ", "The Plant Journal", Jun. 1996, pp. 809-818, vol. 9, No. 6.

Kunkel, Tim, et al., "Inducible isopentenyl transferase as a high-efficiency marker for plant transformation", "Nat. Biotechnol.", Sep. 1999, pp. 916-918, vol. 17, No. 9.

Liu, X.J., et al., "Cis regulatory elements directing tuber-specific and sucrose-inducible expression of a chimeric class I patatin . . . ", "Mol. Gen. Genet.", Sep. 1990, pp. 401-406, vol. 223, No. 3.

Mannino, Raphael J., et al., "Liposome Mediated Gene Transfer", "BioTechniques", Jul./Aug. 1988, pp. 682-690, vol. 6, No. 7.

Odell, Joan T., et al., "Identification of DNA sequences required for activity of the cauliflower mosaic virus 35S promoter", "Nature", Feb. 28, 1985, pp. 810-812, vol. 313, No. 6005.

Potrykus, Ingo, "Gene Transfer to Cereals: An Assessment", "Biotechnology (N.Y.)", Jun. 1990, pp. 535-542, vol. 8, No. 6.

Radke, S.E., et al., "Transformation of *Brassica napus* L. using *Agrobacterium tumefaciens*: developmentally regulated expression of a . . . ", "Theor. Appl. Genet.", May 1988, pp. 685-694, vol. 75, No. 5.

Sambrook, Joseph, et al., "Molecular Cloning: A Laboratory Manual, 2nd Ed. (Entire Book)", 1989, Publisher: Cold Spring Harbor Laboratory Press, Published in: Cold Spring Harbor, NY.

Yokoyama, Ryusuke, et al., "The rolC promoter of *Agrobacterium rhizogenes* Ri plasmid is activated by sucrose in transgenic tobacco plants", "Mol. Gen. Genet.", Jan. 1994, pp. 15-22, vol. 244, No. 1.

* cited by examiner

Fig. 2

```
atggcttcca aaccttttct atctttgctt tcactttcct tgcttctctt tacaagcaca     60

tgttta gca gct gat gtg cag ctg gtg gag tct ggg gga ggc tta gtg       108
       Ala Ala Asp Val Gln Leu Val Glu Ser Gly Gly Gly Leu Val
       1               5                   10

cag cct gga ggg tcc cgg aaa ctc tcc tgt gca gcc tct gga ttc act      156
Gln Pro Gly Gly Ser Arg Lys Leu Ser Cys Ala Ala Ser Gly Phe Thr
15                  20                  25                  30

ttc agt agc ttt gga atg cac tgg gtt cgt cag gct cca gag aag ggg      204
Phe Ser Ser Phe Gly Met His Trp Val Arg Gln Ala Pro Glu Lys Gly
                35                  40                  45

ctg gag tgg gtc gca tat att agt agt ggc agt agt acc atc tac tat      252
Leu Glu Trp Val Ala Tyr Ile Ser Ser Gly Ser Ser Thr Ile Tyr Tyr
            50                  55                  60

gca gac aca gtg aag ggc cga ttc acc atc tcc aga gac aat ccc aag      300
Ala Asp Thr Val Lys Gly Arg Phe Thr Ile Ser Arg Asp Asn Pro Lys
        65                  70                  75

aac acc ctg ttc ctg caa atg acc agt cta agg tct gag gac acg gcc      348
Asn Thr Leu Phe Leu Gln Met Thr Ser Leu Arg Ser Glu Asp Thr Ala
    80                  85                  90

atg tat tac tgc gca aga gat tac ggg gct tat tgg ggc caa ggg acc      396
Met Tyr Tyr Cys Ala Arg Asp Tyr Gly Ala Tyr Trp Gly Gln Gly Thr
95                  100                 105                 110

acg gtc acc gtc tcc tca ggt gga ggc ggt tca ggc gga ggt ggc tct      444
Thr Val Thr Val Ser Ser Gly Gly Gly Gly Ser Gly Gly Gly Gly Ser
                115                 120                 125

ggc ggt ggc gga tcg gac att gag ctc acc cag tct cca gca atc atg      492
Gly Gly Gly Gly Ser Asp Ile Glu Leu Thr Gln Ser Pro Ala Ile Met
            130                 135                 140

tct gca tct cca ggg gag aag gtc acc atg acc tgc agt gcc agt tca      540
Ser Ala Ser Pro Gly Glu Lys Val Thr Met Thr Cys Ser Ala Ser Ser
        145                 150                 155

agt gta agg tac atg aac tgg ttc caa cag aag tca ggc acc tcc ccc      588
Ser Val Arg Tyr Met Asn Trp Phe Gln Gln Lys Ser Gly Thr Ser Pro
    160                 165                 170

aaa aga tgg att tat gac aca tcc aaa ctg tct tct gga gtc cct gct      636
Lys Arg Trp Ile Tyr Asp Thr Ser Lys Leu Ser Ser Gly Val Pro Ala
175                 180                 185                 190

cgc ttc agt ggc agt ggg tct ggg acc tct tac tct ctc aca atc agc      684
Arg Phe Ser Gly Ser Gly Ser Gly Thr Ser Tyr Ser Leu Thr Ile Ser
                195                 200                 205

agc atg gag gct gaa gat gct gcc act tat tac tgc cag cag tgg agt      732
Ser Met Glu Ala Glu Asp Ala Ala Thr Tyr Tyr Cys Gln Gln Trp Ser
            210                 215                 220

agt aat cca ctc act ttc ggt gct ggg acc aag ctg gag ctg aaa cgg      780
Ser Asn Pro Leu Thr Phe Gly Ala Gly Thr Lys Leu Glu Leu Lys Arg
        225                 230                 235

gcg gcc gca gaacaaaaac tcatctcaga agaggatctg aatggatcca              829
Ala Ala Ala
    240

aagacgaact ctag                                                      843
```

METHOD OF INCREASING THE CONTENT OF SELECTED TRANSGENE-CODED PROTEINS OR PEPTIDES IN PLANTS

CROSS-REFERENCE TO RELATED APPLICATIONS

This application is filed under the provisions of 35 U.S.C. §371 and claims the priority of International Patent Application No. PCT/EP02/14512 filed Dec. 18, 2002, which in turn claims priority of European Patent Application No. 01 130319.5 filed Dec. 19, 2001.

FIELD OF THE INVENTION

The present invention relates to a method of increasing the transgene-coded biomolecule content in organisms, in particular in plants. The method is based on a change in the distribution of ATP and/or ADP in cells of the organism which can be carried out by various procedures.

BACKGROUND OF THE INVENTION

Both naturally occurring and synthetic proteins, peptides and nucleic acids have highly interesting properties as regards to their uses as active substances and materials, but are often only available in very small amounts. Since it is also often not possible to obtain them efficiently under economic conditions and in sufficient amounts in recombinant host systems, e.g. in bacteria, such as *Escherichia coli, Bacillus subtilis*, etc., commercial use cannot be realized. In order to be able to obtain more complex proteins and peptides or nucleic acids which are difficult to produce or cannot be produced at all in lower organisms, cells of higher organisms having an inherent complex protein and nucleic acid biosynthesis machinery are increasingly required as host cells. Transgenic animals, plants, mosses, algae, etc. have offered themselves as new recombinant hosts for some years now. Due to the availability of increasing numbers of well characterized biomolecules from molecular research, use of such hosts is gaining in importance for their production.

However, in host organisms the content of transgene-coded biomolecules does not always lie within the desired range. In particular the yields obtained in the host cells for the production of proteins or nucleic acids on an industrial scale are insufficient. On the one hand, this is due to the regulation of gene expression and, on the other hand, also caused by a degradation of the transgenic products by the host organism. In general, an increase in the expression and an increase in the amount of biomolecules stored in the organism is desirable for increasing the content of transgenic proteins, peptides and nucleic acids. This could raise the efficiency of the production of biomolecules in transgenic organisms and subsequently facilitate their recovery and purification.

In order to obtain a high content of transgene-coded biomolecules, it is necessary to make use of those regulation mechanisms resulting in an increase of expression and to avoid or eliminate those suppressing the production or degrading the products. The use of strong promoters is a general approach for increasing transcription and thus raising the amount of mRNA made. This is usually also accompanied by an increase in the amount of foreign protein formed.

In order to protect once formed mRNA from an increased turnover, which plays a role in gene silencing, all measures preventing detection of RNA as foreign are suited. Such measures are e.g. the prevention of double-stranded RNA formation, the adaptation of the GC content to that of the host cell and the use of repressor proteins for suppressing post-translational gene silencing (De Wilde, Plant Molecular Biology 545 (2000), 347-359). By adapting the codon usage to that of the host cell it is possible to achieve an increase in translation. The transgene-coded biomolecule content can also be raised by lowering the formation of an endogenous storage protein, as accomplished by Goossens et al., (FEBS Letters 456 (1999), 160-164) by means of the antisense technology. Another possibility of raising the foreign protein expression in transgenic organisms is the construction of fusion proteins between the target proteins and e.g. chaperonins or chaperonin binding domains.

However, it has only been possible thus far to raise the content of the desired transgenic molecules in organisms to some degree by these methods. In order to render the production of biomolecules in transgenic organisms more efficient, a mechanism is highly required which can be used as such or also in addition to said methods and in this connection raises the transgenically encoded biomolecule content significantly.

The present invention is thus based on the technical problem of providing a means by which an increase in the transgenic biomolecule content can be achieved in organisms, in particular in plants.

SUMMARY OF THE INVENTION

This technical problem is solved by the subject matters defined in the claims. The present invention comprises a novel mechanism of increasing the transgene-coded biomolecule content in organisms, such as plants, which is based on influencing the energy metabolism of the cells. It has been found surprisingly that a physiological change can be caused by modifying the distribution of ATP or ADP in the cell so as to achieve a significantly higher content of transgenically coded products in cells of the organism.

ATP is the universal energy carrier of all live cells. Energy in the form of ATP is required for almost all anabolic pathways. In heterotrophic plant cells, ATP is mainly synthesized by means of oxidative phosphorylation in the mitochondria from ADP and inorganic phosphate. Under anaerobic conditions, this is done by means of substrate-level phosphorylation in the cytosol. ATP is transported out of the mitochondria via the mitochondrial ADP/ATP transport protein which is one of the best studied membrane proteins. The mitochondrial ADP/ATP transport protein catalyzes exclusively the ATP export in return for the import of ADP.

In the case of heterotrophic vegetable storage tissues a comparatively large amount of ATP is taken up into the storage plastids to energize biosynthesis steps only occurring there, such as starch or fatty acid biosynthesis. This uptake is catalyzed by a plastidiary ATP/ADP transport protein which is localized in the inner coat membrane and enables the ATP uptake in return for the ADP release.

In order to analyze the effect of modified plastidiary ATP/ADP transporter activities on the carbohydrate balance, transgenic potato plants having increased or reduced transporter activity were produced in the experiments resulting in the present invention.

The amount of endogenous plastidiary ATP/ADP transporter in potatoes (AATP1, *Solanum tuberosum* St) was reduced by means of antisense inhibition. Part of the AATP1, St-coding cDNA was introduced in antisense orientation into the potato genome. This cDNA was controlled by the constitutive CaMV 35S promoter. Various independent lines having in each case individually reduced activity of the plastidiary ATP/ADP transporter being obtained. The activity of the plastidiary ATP/ADP transporter was thus reduced to 64% to 79% as compared to that of non-transgenic control plants. The transgenic potato plants showed no phenotypic changes in the region of the aboveground green tissues. In contrast thereto, the morphology of the tubers was markedly altered (branched tubers) and the starch content dropped to about 50% as compared to the non-transgenic control plants (Tjaden et al., Plant Journal, 16 (1998), 531-540). Summarized, due to the reduced ATP/ADP transporter activity comparatively less ATP was taken up into the plastids and consequently less starch was produced.

Furthermore, transgenic potato plants having an increased activity of the plastidiary ATP/ADP transporter were produced by introducing the cDNA for the plastidiary ATP/ADP transporter from *Arabidopsis thaliana* (AATP1,AT) in sense orientation into the potato genome under the control of the 35S promoter. This led to various independent lines each having individually increased activity of the plastidiary ATP/ADP transporter. The measured activity of the plastidiary ATP/ADP transporter was between 130 and 148% in the various lines as compared to those in non-transgenic control plants. The transgenic potato plants showed no phenotypic changes in the region of the aboveground green tissues. However, the starch content in the tubers was increased by up to about 150% as compared to the control (Tjaden et al., supra). Summarized, due to the increased ATP/ADP transporter activity comparatively more ATP was taken up into the plastids and therefore more starch was produced.

There is reason to suppose that the change in the ATP or ADP concentrations in certain parts of a plant cell has considerable effects on the cell metabolism and the regulation of genes. It was thus investigated in the studies conducted in connection with the present invention whether such a change also influences the protein content in the plant cells. For this purpose, transgenic potato plants of the Desirée variety were produced e.g. by means of the gene constructs described in Tjaden et al. (supra) to either reduce via "antisense" or increase via "sense" constructs the ATP/ADP transporter activity. The resulting transgenic plants were partially hypertransformed using another transgene. The plants obtained were subjected to a proteinchemical analysis, and the content of different foreign proteins and whole protein in tuber extracts was determined. It turned out that there was a marked increase in the foreign protein content in transgenic plants (cf. below Examples 1-2).

Thus, the present invention relates to a method of increasing the transgene-coded biomolecule content in organisms, prefeably in plants, which is characterized by changing the distribution of ATP and/or ADP in cells of the organisms (as compared to the original situation).

An increase in the content of transgene-coded biomolecules is understood to mean every increase in the concentration of said biomolecules in an extract obtained from the tissues of the transgenic organisms as compared to the content in an extract obtained from organisms which do not show the change in the distribution of ATP and/or ADP in the cells according to the present invention. For example, this increase can be effected by an enhanced accumulation of the biomolecules in one or more cell compartments, such as the endoplasmic reticulum, the plastids, the vacuoles, the lysosomes, the mitochondria, the cell nucleus, the Golgi apparatus, the peroxisomes, the cytosol and others. In a preferred embodiment of the described method, the content of transgene-coded biomolecules is raised selectively, the content of endogenous biomolecules in cells of the organisms being not changed significantly. This increase can be constitutive or regulated temporally, locally or inducibly.

Within the meaning according to the present invention the transgene-coded biomolecules relate to both proteins and peptides as well as to nucleic acid molecules. In particular peptides, proteins and nucleic acids which are not expressed naturally in the respective target organism are mentioned. However, peptides, proteins and nucleic acids which are not expressed naturally in their present form are also transgene-coded biomolecules. They include e.g. all forms of modified or non-native proteins, peptides and nucleic acids such as hybrid proteins, chimeric proteins and chimeric nucleic acid constructs. Fragments of proteins, peptides or nucleic acids also represent transgenic biomolecules within the meaning according to the present invention. In particular proteins, peptides or nucleic acids whose expression pattern was modified in the respective host organism shall also be transgenically encoded biomolecules within the meaning according to the invention. Examples thereof are proteins, peptides and nucleic acids whose expression is not regulated naturally in the present form. For example, the natural expression thereof can be regulated temporally, locally or inducibly in another way. In particular, the change of the expression of the sequences coding for the biomolecules can also show as an increase or reduction of the expression rate. Nucleic acids are in particular all deoxyribonucleic acids and ribonucleic acids. They are preferably available as ribozymes, single-stranded or double-stranded oligonucleotides or also as relatively long-chain nucleic acid molecules. Particularly preferred proteins are antibodies, aptamers, receptors, enzymes, growth factors, hormones and specific antigen molecules for use in diagnosis, therapy and the prevention of diseases, such as viral diseases or cancerous diseases. Such proteins may be e.g. interferons, immunoglobulins, growth hormones, insulin, collagen, plasminogen activator, blood factors such as factors I to XII, histocompatibility antigens, enzymes, tumor marker proteins and antibodies specific thereto as well as viral antigens and antibodies specific thereto.

The organisms suitable for use in the method according to the invention may contain one or more transgenes and express them in parallel or sequentially. The parallel expression of several transgenes is conceivable via the control of the coding sequences by constitutive and/or inducible promoters. A sequential expression can be achieved by the regulation of the gene expression of several transgenes in an organism, which can be induced in different ways.

The organisms suitable for the method according to the invention are animals, humans and plants. The term "animals" as used herein comprises preferably mammals, e.g. cows, horses, goats, sheeps, pigs, mice, rats and rabbits. The plants may, in principle, be plants of any species, i.e. both monocotyledonous and dicotyledonous plants. The term "plants" as used herein comprises preferably gramineae, chenopodiacea, leguminousea, brassicaceae, solanaceae, fungi, mosses, and algae. Crop plants, e.g. plants such a wheat, barley, rice, corn, sugar beets, sugarcane, rape, mustard, oilseed rape, flax, safflower, peas, beans, lupins, tobacco, lucerne, soya, bananas, ananas, potatoes, sunflowers, melons, sweet potatoes, spelt, alfalfa, paprika, topinambur, tomatoes, durum wheat or rye are particularly preferred.

In a preferred embodiment, the method according to the invention is characterized in that the activity or concentration of a protein involved in the subcellular distribution of ATP and ADP is increased or reduced in the organism. This protein is usually a protein which is naturally available in the corresponding organism, e.g. the mitochondrial ADP/ATP transport protein, the plastidiary ATP/ADP transporter or the plastidiary triose phosphate/phosphate transporter. A particularly preferred embodiment of the method according to the invention is one in which the expression of a gene which codes for a protein involved in the subcellular distribution of ATP and ADP is increased or reduced. This gene expression can be modified by methods known to a person skilled in the art. For example, this can be effected by the above changes in the protein concentration and those described in the examples using antisense or sense constructs. A change in the protein activity or concentration can basically be effected via both gene expression and a functional inhibition of the protein activity, e.g. by the expression of binding, inhibiing, neutralizing or catalytic antibodies or other specifically binding and blocking proteins or peptides, by ribozymes, single-stranded or double-stranded oligonucleotides, aptamers, lipids, natural receptors, lectins, carbohydrates, etc.

In the method according to the invention the ATP or ADP concentration in cell compartments can also be influenced by introducing a protein (polypeptide) which is not naturally available in the respective organism. In order to obtain the localization of the protein in the desired cell compartment it may be favorable for the protein to have a signal peptide, so that it can be transported into certain cell compartments of a plant cell. The person skilled in the art is familiar with suitable signal peptides and methods of linking the signal peptides with a desired protein. For example, reference is made to the signal peptide of amylase from barley as to the apoplast (Düring et at., Plant Journal 3 (1993), 587-598), to a murine signal peptide, to the combination or murine signal peptide and the KDEL (SEQ ID NO: 1) KDEL-ER retention signal as regards ER (Artsaenko et at., Molecular Breeding 4 (1998), 313-319), to the targeting signal of a mammal-alpha-2,5-sialyltransferase regarding the Golgi apparatus (Wee et al., Plant Cell IV (1998), 1759-1768), to the vacuolar localizing signal of a vacuolar chitinase from cucumber as regards the vacuoles (Neuhaus et at., Proc. Natl. Acad. Sci. U.S.A. 88 (1991), 10362-10366), to the ferredoxin transit peptide as to the chloroplasts and plastids, and to the transit peptide of tryptophanyl tRNA synthethase from yeast regarding the mitochondria (Schmitz and Lonsdale, Plant Cell 1 (1998), 783-791). Basically, the protein involved in the subcellular distribution of ATP and APD can be administered by various methods, e.g. via media, such as the culture media, of a plant or of parts thereof, in particular plant cells. However, as pointed out above already, it is preferred to administer the protein to plants or parts thereof in the form of a nucleic acid coding for it, e.g. DNA or RNA. For this purpose, it is necessary for the nucleic acid to be available in an expression vector or to be ligated with sequences thereof. In this connection, it can be favorable for this vector or these sequences to enable an expression of the nucleic acid in cell compartments. Such expression vectors or sequences are known to the person skilled in the art. For example, reference is made to Svab et al., Proc. Natl. Acad. Sci. U.S.A. 87 (1990), 8526-8530; Khan and Maliga, Nature Biotechnology 17 (1999), 910-915; and Sidorov et al., Plant Journal 19 (1999), 209-216.

Methods of constructing the expression vectors containing the desired gene, e.g. for a plastidiary ATP/ADP transporter from *Arabidopsis thaliana* (AATP1,At) in expressible form are known to the person skilled in the art and also described in common standard works (cf. e.g. Sambrook et al., 1989, Molecular Cloning, A Laboratory Manual, $2^{nd}$ edition, Cold Spring Harbor Laboratory Press, Cold Spring Harbor, N.Y.). The expression vectors can be based on a plasmid, cosmid, virus, bacteriophage or another vector common in genetic engineering. These vectors may have further functional units which effect stabilization of the vector in the plants, for example. If used for plants they may contain left-border and right-border sequences of agrobacteria T-DNA so as to enable stable integration into the genotype of plants. A termination sequence may also be present which serves for the correct termination of transcription and the addition of a poly-A sequence to the transcript. Such elements are described in the literature (cf. Gielen et al., EMBO J. 8 (1989), 23-29) and can be exchanged as desired.

The person skilled in the art is familiar with suitable promoters for the expression of the gene coding for the desired protein. The promoters include e.g. the cauliflower mosaic virus 35S promoter (Odell et al., Nature 313 (1995), 810-812), the *Agrobacterium tumefaciens* nopaline synthase promoter and the mannopine synthase promoter (Harpster et al., Molecular and General Genetics 212 (1988), 182-190).

The increase or decrease of the above-described protein activities can be effected constitutively or temporally, locally or be induced by certain stimuli. A temporally or locally limited or inducible increase or decrease of the protein activities also suppresses the changes in the tuber morphology, described by Tjaden et al. (supra).

Thus, another preferred embodiment of the method according to the invention is characterized in that the expression of the gene whose product causes a change in the distribution of ATP and/or ADP in cells of the organism is regulated in the organism temporally, locally or inducibly. For example, the gene coding for the desired protein can be linked with an inducible promoter, which permits e.g. the control of the synthesis of the desired protein, e.g. in a plant, at a desired time. Suitable promoters are known to the person skilled in the art and they comprise e.g. the anaerobically inducible Gap C4 promoter from corn (Bülow et al., Molecular Plant-Microbe Interactions 12 (1999), 182-188), PR promoters such as L-phenylalanine ammonium lyase, chalcone synthase and hydroxyproline rich glycoprotein promoters, inducible by ethylene (Ecker and Davies, Proc. Natl. Acad. Sci. U.S.A. (1987), 5202-5210) and a dexamethasone-inducible chimeric transcription induction system (Kunkel et al., Nature Biotechnology 17 (1990), 916-918), the IncW promoter from corn inducible by saccharose or D-glucose (Chen et al., Proc. Natl. Acad. Sci. U.S.A. 96 (1999), 10512-10517). Reference is also made to Dalta et al., Biotechnology Annual Review 3 (1997), 269-290, and Gatz and Denk, Trends in Plant Science 3 (1998), 352-358. Furthermore, promoters are suited which permit local regulation of the expression, i.e. only in certain plant parts or organs. Such promoters are e.g. the patatin promoter from potato (Liu et al., Molecular and General Genetics 223 (1990), 401-406)(tuber-specific), the napin promoter from allseed rape (Radke et al., Theoretical and Applied Genetics 75 (1988), 685-694) (embryo-specific in the seed), the RolC promoter from *Agrobacterium rhizogenes* (Yokoyama et al., Molecular and General Genetics 244 (1994), 15-22) (phloem-specific), the TA29 promoter from tobacco (Kriete et al., Plant Journal 9 (1996), 809-818) (tapetum-specific), the LeB4 promoter from *Vicia faba* (Bäumlein et al., Molecular and General Genetics 225 (1991), 121-128) (seed-specific) and the rbcS and cab promoters from petunia (Jones et al., Molecular and General Genetics 212 (1988), 536-542) (leaf-specific or limited to photosynthetically active tissues).

In another preferred embodiment of the method according to the invention the expression of the plastidiary ATP/ADP transporter is raised or lowered. In this connection, the expression can be lowered by introducing an antisense construct suppressing the expression of the endogenous gene, and the expression can be raised by introducing a sense construct. The sense construct may be a gene available on an expression vector for the endogenous transporter e.g. under the control of a strong promoter but also a heterologous gene which codes for a transporter from another organism, preferably a closely related organism.

A large number of cloning vectors which contain a replication signal for *E. coli* and a marker gene for the selection of transformed bacterial cells are available for the production of the expression vectors which shall be introduced into plants. Examples of such vectors are pBR322, pUC series, M13mp series, pA-CYC184, etc. The desired sequence may be introduced into the vector at an appropriate restriction site. The resulting vector is used for the transformation of *E. coli* cells. Transformed *E. coli* cells are cultured in a suitable medium, then harvested and lysed. The vector is then recovered. In general, restriction analyses, gel electrophoresis and further biochemical and molecular-biological methods are used as analytical methods for characterizing the vector DNA obtained. The vector DNA can be cleaved after every manipulation and the DNA fragments obtained can be linked with other DNA sequences. Each vector DNA sequence can be cloned into the same or into other vectors.

A number of methods are available for the introduction of the above expression vectors into a plant cell. These methods comprise transformation of plant cells with T-DNA using *Agrobacterium tumefaciens* or *Agrobacterium rhizogenes* as trans formation means, fusion of protoplasts, injection, electropo ration of DNA, introduction of DNA using the biolistic method and further possibilities.

The injection and electroporation of DNA in plant cells do generally not make special demands on the vectors used. It is possible to use simple plasmids such as pUC derivatives. However, if whole plants shall be regenerated from cells transformed in this way, a selectable marker should be present. Suitable selectable markers are known to the person skilled in the art and they comprise e.g. the neomycin phosphotransferase II gene from *E. coli* (Beck et al., Gene 19 (1982), 327-336), the sulfonamide resistance gene (EP-369637), and the hygromycin resistance gene (EP-186425). Depending on the method of introducing the desired gene into the plant cell, further DNA sequences may be required. For example, if the Ti or Ri plasmid is used for the transformation of the plant cell, at least the right border, but often the right and left borders, of the Ti and Ri plasmid T-DNA must be connected as a flanking region with the genes to be introduced.

If agrobacteria are used for the transformation, the DNA to be introduced must be cloned into special vectors, i.e. into either an intermediary vector or a binary vector (cf. the below examples). Due to sequences homologous to sequences in the T-DNA, the intermediary vectors can be integrated into the Ti or Ri plasmid of the agrobacteria by homologous recombination. It also contains the vir region necessary for the T-DNA transfer. Intermediary vectors cannot replicate in agrobacteria . By means of a helper plasmid, the intermediary vector can be transferred to *Agrobacterium tumefaciens*. Binary vectors can replicate in both *E. coli* and *Agrobacterium*. They contain a selection marker gene and a linker or polylinker, which are surrounded by the right and left T-DNA border. They can be transformed directly into the agrobacteria. The *agrobacterium* serving as a host cell should contain a plasmid which carries a vir region. The vir region is necessary for the transfer of T-DNA into the plant cell. Additional T-DNA may be present. The *agrobacterium* transformed in this way is used for the transformation of plant cells.

In order to transfer the DNA into the plant cell, plant explants can usefully be cocultured with *Agrobacterium tumefaciens* or *Agrobacterium rhizogenes*. Whole plants can then be regenerated again from the infected plant material (e.g. leaf portions, stem segments, roots, but also protoplasts or suspension-cultured plant cells) in a suitable medium which may contain antibiotics or biocides for the selection of transformed cells. The resulting plants can subsequently be studied for the presence of the introduced DNA. Alternative systems for the transformation of monocotyledonous plants are transformation by means of a biolistic approach, electrically or chemically induced DNA uptake into protoplasts, electroporation of partially permeabilized cells, macroinjection of DNA into inflorescences, microinjection of DNA into microspores, oocytes and pro-embryos, DNA uptake by germinating pollens, and DNA uptake into embryos by swelling (for an overview see Potrykus, Biotechnologie 8 (1990), 535-542). While the transformation of dicotyledonous plants is well established via Ti plasmid vector systems using *Agrobacterium tumefaciens*, more recent studies indicate that monocotyledonous plants are also very well accessible to transformation by means of vectors based on *Agrobacterium.*

In a preferred embodiment, the expression vectors used according to the invention contain localization signals for localization in cell compartments, in particular in endoplasmic reticulum (ER), apoplasts, Golgi apparatus, plastids, peroxisomes, mitochondria and/or vacuoles. Reference is made to the above statements on the signal peptides. The KDEL (SEQ ID NO: 1) KDEL-ER targeting peptide, the Golgi localization signal of β-1,2-N-acetylglucosamine transferase (Gntl), the transit peptide from the small subunit of ribulose bisphosphate carboxylase and/or the vacuolary targeting signal SKNPIN (SEQ ID NO: 2) are particularly preferred as localization signals.

In principle, the plant portions desired for the expression of the transgene relate to any plant part, in any case to replication material of these plants, e.g. seeds, tubers or bulbs, rootstocks, seedlings, cuttings, etc.

In principle, the present invention also enables an increase in the expression of transgenes in animals and humans. For this purpose, the above protein can be administered as such or in combination with a signal peptide to animals, humans or cells thereof. Such a signal peptide can be e.g. a murine signal peptide, a combination of a murine signal peptide and the KDEL-ER retention signal, or the targeting signal of a mammalian alpha-2,6-sialyltransferase as regards the Golgi apparatus. Furthermore, the protein can be administered in the form of a nucleic acid coding for it, e.g. DNA or RNA, to animals, humans or cells thereof. Administration in the form of a nucleic acid requires that the latter is present in an expression vector or is ligated with sequences thereof. Reference is made to the above general statements on expression vectors and their production. In addition, reference is made to vectors which are suited for the gene therapy in animals and humans. In them, the nucleic acid can be controlled by an inducible or tissue-specific promoter, such as metallothionein I or polyhedrin promoter. Preferred vectors are e.g. viruses, such as retroviruses, adenoviruses, adeno-associated viruses or vaccinia viruses. Examples of retroviruses are MoMuLV, HaMuSV, MUMTV, RSV or GaLV. Furthermore, the nucleic acid coding for the polypeptide can be transported to the target cells in the form of colloidal dispersions. They comprise e.g. liposomes and lipoplexes (Mannino et al., Biotechniques 6 (1988), 682).

According to the invention, the above protein is administered to humans and cells. In principle, the animals may belong to any animal species. They are preferably useful and domestic animals, e.g. cattle, horses, sheep, pigs, goats, chickens, turkeys, dogs, cats, etc.

Examples of transgenes whose expression in animals and humans can be raised are in particular peptides, proteins and nucleic acids. The particularly preferred proteins are antibodies, aptamers, receptors, enzymes, growth factors, hormones and specific antigen and antibody molecules for use in diagnosis, therapy and the prevention of both viral diseases and cancerous diseases. Such proteins are e.g. interferons, immunoglobulins, growth hormones, insulin, collagen, plasminogen activator, blood factors such as factors I to XII, histocompatibility antigens, enzymes, tumor marker proteins and antibodies specific thereto as well as viral antigens and antibodies specific thereto. Examples of nucleic acids are single-stranded and double-stranded RNA or DNA, oligonucleotides and ribozymes.

BRIEF DESCRIPTION OF THE FIGURES

FIG. 1 shows the NptII protein content in ng/ml in the extract of potato tubers. The lines MBP7sATPT contain the sense gene construct for the plastidiary ATP/ADP translocator from *Arabidopsis thaliana* in transgenic potato plants of the Désirée variety. The lines MPB/aATPT contain the antisense gene construct for the plastidiary ATP/ADP translocator from *Arabidopsis thaliana* in transgenic potato plants of the Désirée variety. Désirée: non-transgenic starting variety Désirée as a control. DK1: transgenic control line var. Désirée only containing the Npt II gene under control of the NOS promoter.

FIG. 2

FIG. 2 shows the DNA sequences of the primers used and an svFv antibody used according to the invention.

DETAILED DESCRIPTION OF THE INVENTION

Figure 1:
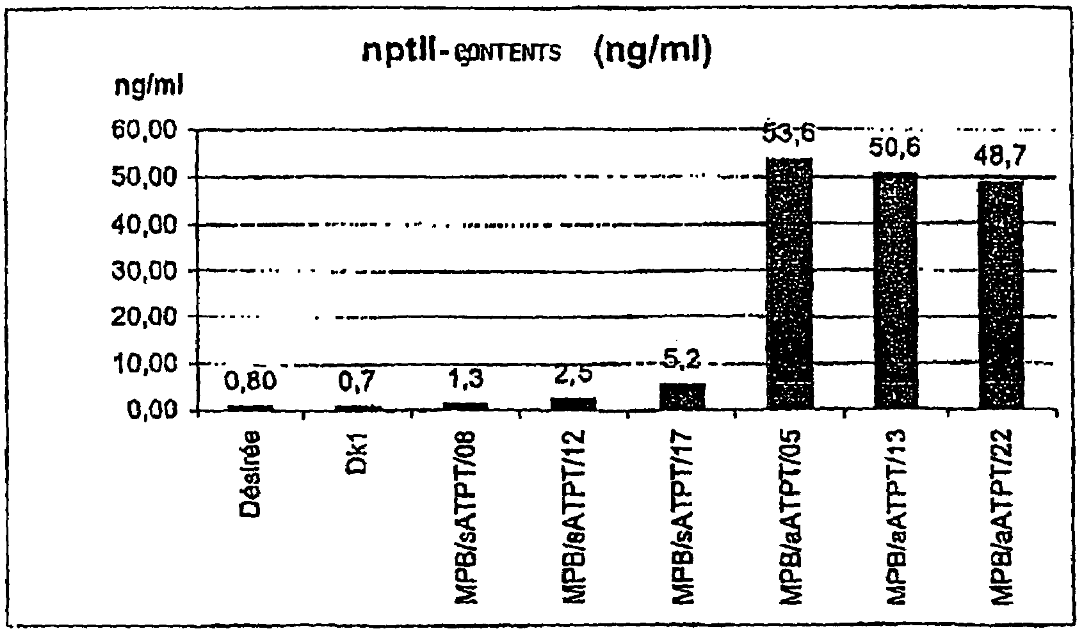
FIG. 1

The invention is explained by the following examples.

EXAMPLE 1

Increase in the Expression of Npt II in Transgenic Potato Tubers

The gene constructs described in Tjaden et al. (supra) for "antisense" decrease ("MPB/aATPT") or "sense" increase ("MBP/sATPT") of the plastidiary ATP/ADP transporter activity in potato tubers were each ligated blunt-end into the opened and filled-in singular HindIII restriction site of the binary vector pSR 8-30 (cf. Düring et al., supra; Porsch et al., Plant Molecular Biology 37 (1998), 581-585). The two transformation vectors pSR8-30/sATPT were obtained. These two expression vectors were used separately for the transformation of *E. coli* SM 10. Transformants were mixed with *Agrobacterium GV* 3101 and incubated at 28° C. overnight. (Koncz and Schell, Mol. Gen. Genet. 204 (1986); 383-396, Kocz et al., Proc. Natl. Acad. Sci. U.S.A., 84 (1987), 131-135). Selection was made on carbenicillin, the bla gene necessary for this purpose being available in the above expression vectors. Selected clones of *Agrobacterium tumefaciens* were applied onto detached leaves, cut several times at the middle rib, of potato plants cv. Désirée and the leaves were incubated at 20° C. in the dark for 2 days. Thereafter, the agrobacteria were washed off and plant growth substances were added to the potato leaves, so that preferably shoots regenerated. Furthermore, non-transformed cells were killed in the potato leaves by the addition of kanamycin to the plant medium. Growing shoots were cut off and were allowed to grow roots in the medium without plant growth substances but with kanamycin. The further cultivation of the potato plants was performed as usual. On the one hand, transgenic lines including the antisense gene construct and, on the other hand, transgenic lines including the sense gene construct were obtained. The regenerated potato lines were planted in soil and grown in a greenhouse. After the ripening of the potato plants, the tubers were harvested and stored for the protein-chemical studies.

In order to study the antisense effect on the foreign gene expression, the NptII content in tuber extracts of all lines was compared by means of ELISA, since apart from Desiree all transgenic lines express the Npt II gene under the control of the nos promoter. The detection limit in the sandwich ELISA is at 0.5 ng Npt II/ml extract. The results show that the antisense lines MPB/aATPT/05, MPB/aATPT/13 and MPB/aATPT/22 contain Npt II concentrations which are 9 to 10 times as high as the content of the control. The determined Npt II values are about 0.7 ng/ml in the control DK1 and thus at the same order as those of the sense plants.

It showed that a major increase of the Npt II gene expression could be effected in transgenic potato tubers by using the described antisense constructs according to the invention.

EXAMPLE 2

Increase in the Expression of scFv Antibodies in Transgenic Potato Tubers

For this test, the plants described in Example 1 were hypertransformed with a gene construct which codes for an scFv antibody. The binary vector pLH9000Hyg was obtained by removing by means of restriction digest with XbaI and SpeI the kanamycin resistance-mediating expression cassette of the binary vector pLH9000 (L. Hausmann and R. Töpfer, *Vorträge Pflanzenzüchtung* [Lectures on Plant cultivation] 45 (1999) 155-172). In its place, a hygromycin resistance-mediating expression cassette was inserted which had been produced by amplification by PCR with primers

```
TCT AGA GAT CAT GAG CGG    (SEQ ID NO: 3)
AGA ATT AA
and

ACT AGT AAT TCC CAT CTT    (SEQ ID NO: 4)
GAA AGA AA
```

from the binary vector BinHygTOp (GenBank G1:886843) and subsequent restriction digest using XbaI and SpeI. An expression cassette containing the gene (SEQ ID NO: 5) for a single-chain (scFv) antibody (SEQ ID NO: 6) having the sequence shown in FIG. 2 under the control of the CAMV 35S promoter was ligated into the opened SalI restriction site of the binary vector pLH9000Hyg. The transformation vector pLH9000Hyg/scFv was obtained.

This expression vector was used for the transformation of *E. coli* SM10. Transformants were mixed with *agrobacterium* GV 3101 and incubated at 28° C. overnight (Koncz (supra)). Selection was made on streptomycin, the aadA gene necessary for this purpose being present in the above expression vectors. Selection clones of *Agrobacterium tumefaciens* were applied onto detached leaves, cut several times at the middle rib, of the potato plants described in Example 1, and the leaves were incubated at 20° C. in the dark for 2 days. Thereafter, the agrobacteria were washed off and plant growth substances were added to the potato leaves, so that preferably shoots regenerated. Furthermore, non-transformed cells in the potato leaves were killed by the addition of hygromycin to the plant medium. Growing shoots were cut off and were allowed to root on the medium without plant growth substances but with hygromycin. The potato plants were further cultivated as usual. Transgenic lines including the antisense gene construct and the scFv gene construct, transgenic lines including the sense gene construct and the scFv gene constructs, and transgenic lines which only included the scFv gene construct were obtained. The regenerated potato lines were planted in soil and grown in a greenhouse. After the ripening of the plants, the resulting potato tubers were stored until the protein-chemical study was conducted.

In order to study the antisense effect on the foreign protein content, the content of scFv in extracts of potato tubers of all lines was compared by means of ELISA. The detection limit in the sandwich ELISA is at 500 ng scFv/ml extract. The results show that the antisense lines MPB/aATPT/05/scFv/05, MPB/aATPT/05/scFv/08 and MPB/aATPT/05/scFV/12 contain scFv concentrations which are 5 to 10 times as high as the content of the sense lines.

A major increase in the expression of the scFv gene in transgenic potato plants could be effected by using the described antisense constructs according to the invention.

The invention claimed is:

1. A method of increasing the content of one or more transgene-coded proteins or peptides in a transgenic potato plant comprising inhibiting a potato plastidary ATP/ADP transporter gene in said plant by antisense inhibition thereof, wherein the potato plant is transformed with and expresses (i) an antisense gene construct for the plastidiary ATP/ADP transporter gene, (ii) a selectable marker gene and (iii) one or more further desired transgenes, wherein the content of the transgene-coded protein or peptide in said transgenic potato plant is increased relative to the content of the transgene-coded protein or peptide in a control plant of the same genetic background.

2. The method according to claim 1, wherein the expression of the transgene-coded proteins or peptides is constitutive or is regulated temporally, locally or inducibly.

3. The method according to claim 1, wherein several transgene-coded proteins or peptides are expressed in parallel or sequentially.

4. The method according to claim 1, wherein the antisense construct suppressing the expression of the plastidiary ATP/ADP transporter is a cDNA of the plastidiary ATP/ADP transporter in antisense orientation.

5. The method according to claim 1, wherein the transgene-coded proteins are under the control of a promoter selected from the group consisting of *Agrobacterium tumefecians* nopaline synthase promoter, cauliflower mosaic virus 35S promoter and mannopine synthase promoter.

6. The method according to claim 1, wherein the one or more further desired transgenes codes for a protein selected from the group consisting of an antibody, a receptor, a growth factor, a hormone, a specific antigen, an interferon, an irnmunoglobulin, a growth hormone, insulin, collagen, plasnilnogen activator, blood factor, a histocompatibility antigen, a tumor marker protein and a viral protein.

7. The method according to claim 1, wherein the expression of the transgene-coded proteins or peptides is increased in transgenic potato tubers.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial
<220> FEATURE:
<223> OTHER INFORMATION: signal polypeptide

<400> SEQUENCE: 1

Lys Asp Glu Leu
1


<210> SEQ ID NO 2
<211> LENGTH: 6
<212> TYPE: PRT
<213> ORGANISM: Artificial
<220> FEATURE:
<223> OTHER INFORMATION: signal polypeptide

<400> SEQUENCE: 2

Ser Lys Asn Pro Ile Asn
1               5


<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3

tctagagatc atgagcggag aattaa                                          26


<210> SEQ ID NO 4
<211> LENGTH: 26
<212> TYPE: DNA
<213> ORGANISM: Artificial
<220> FEATURE:
<223> OTHER INFORMATION: primer

<400> SEQUENCE: 4

actagtaatt cccatcttga aagaaa                                          26


<210> SEQ ID NO 5
<211> LENGTH: 843
<212> TYPE: DNA
<213> ORGANISM: Artificial
<220> FEATURE:
<223> OTHER INFORMATION: scFV-antibody

<400> SEQUENCE: 5

atggcttcca aaccttttct atctttgctt tcactttcct tgcttctctt tacaagcaca     60
```

-continued

```
tgtttagcag ctgatgtgca gctggtggag tctgggggag gcttagtgca gcctggaggg    120

tcccggaaac tctcctgtgc agcctctgga ttcactttca gtagctttgg aatgcactgg    180

gttcgtcagg ctccagagaa ggggctggag tgggtcgcat atattagtag tggcagtagt    240

accatctact atgcagacac agtgaagggc cgattcacca tctccagaga caatcccaag    300

aacaccctgt tcctgcaaat gaccagtcta aggtctgagg acacggccat gtattactgc    360

gcaagagatt acggggctta ttggggccaa gggaccacgg tcaccgtctc ctcaggtgga    420

ggcggttcag gcggaggtgg ctctggcggt ggcggatcgg acattgagct cacccagtct    480

ccagcaatca tgtctgcatc tccaggggag aaggtcacca tgacctgcag tgccagttca    540

agtgtaaggt acatgaactg gttccaacag aagtcaggca cctcccccaa aagatggatt    600

tatgacacat ccaaactgtc ttctggagtc cctgctcgct tcagtggcag tgggtctggg    660

acctcttact ctctcacaat cagcagcatg gaggctgaag atgctgccac ttattactgc    720

cagcagtgga gtagtaatcc actcactttc ggtgctggga ccaagctgga gctgaaacgg    780

gcggccgcag aacaaaaact catctcagaa gaggatctga atggatccaa agacgaactc    840

tag                                                                  843
```

```
<210> SEQ ID NO 6
<211> LENGTH: 241
<212> TYPE: PRT
<213> ORGANISM: Artificial
<220> FEATURE:
<223> OTHER INFORMATION: scFv-antibody

<400> SEQUENCE: 6

Ala Ala Asp Val Gln Leu Val Glu Ser Gly Gly Gly Leu Val Gln Pro
1               5                   10                  15

Gly Gly Ser Arg Lys Leu Ser Cys Ala Ala Ser Gly Phe Tyr Phe Ser
            20                  25                  30

Ser Phe Gly Met His Trp Val Arg Gln Ala Pro Glu Lys Gly Leu Glu
        35                  40                  45

Trp Val Ala Tyr Ile Ser Ser Gly Ser Ser Thr Ile Tyr Tyr Ala Asp
    50                  55                  60

Thr Val Lys Gly Arg Phe Thr Ile Ser Arg Asp Asn Pro Lys Asn Thr
65                  70                  75                  80

Leu Phe Leu Gln Met Thr Ser Leu Arg Ser Glu Asp Thr Ala Met Tyr
                85                  90                  95

Tyr Cys Ala Arg Asp Tyr Gly Ala Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Ile Glu Leu Thr Gln Ser Pro Ala Ile Met Ser Ala
    130                 135                 140

Ser Pro Gly Glu Lys Val Thr Met Thr Cys Ser Ala Ser Ser Ser Val
145                 150                 155                 160

Arg Tyr Met Asn Trp Phe Gln Gln Lys Ser Gly Thr Ser Pro Lys Arg
                165                 170                 175

Trp Ile Tyr Asp Thr Ser Lys Leu Ser Ser Gly Val Pro Ala Arg Phe
            180                 185                 190

Ser Gly Ser Gly Ser Gly Thr Ser Tyr Ser Leu Thr Ile Ser Ser Met
        195                 200                 205

Glu Ala Glu Asp Ala Ala Thr Tyr Tyr Cys Gln Gln Trp Ser Ser Asn
```

-continued

```
    210                 215                 220

Pro Leu Thr Phe Gly Ala Gly Thr Lys Leu Glu Leu Lys Arg Ala Ala
225                 230                 235                 240

Ala
```